(12) United States Patent
Liu et al.

(10) Patent No.: US 8,571,397 B2
(45) Date of Patent: Oct. 29, 2013

(54) AUTO FOCUS INTRAORAL CAMERA WITH LIQUID LENS

(75) Inventors: Zhaohua Liu, YangPu (CN); Tan Wang, Pudong (CN); Jiwu Zhang, Pudong (CN)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 13/129,883

(22) PCT Filed: Nov. 21, 2008

(86) PCT No.: PCT/CN2008/001900
§ 371 (c)(1),
(2), (4) Date: May 18, 2011

(87) PCT Pub. No.: WO2010/057336
PCT Pub. Date: May 27, 2010

(65) Prior Publication Data
US 2011/0222841 A1 Sep. 15, 2011

(51) Int. Cl.
*A61B 3/14* (2006.01)
*G03B 13/34* (2006.01)
*G02B 26/02* (2006.01)

(52) U.S. Cl.
USPC ............. 396/16; 396/133; 359/228; 359/291; 348/66; 348/77

(58) Field of Classification Search
USPC ............ 396/16, 106, 133, 529; 359/228, 245, 359/252, 290, 291; 382/128; 348/66, 77
See application file for complete search history.

(56) References Cited

U.S. PATENT DOCUMENTS

| 3,599,548 A | 8/1971 | Hennig |
| 4,199,425 A | 4/1980 | Sinkevitch |
| 5,923,908 A | 7/1999 | Schrock et al. |
| 6,369,954 B1 | 4/2002 | Berge et al. |
| 6,449,081 B1 | 9/2002 | Onuki et al. |
| 7,010,223 B2 | 3/2006 | Thoms |

(Continued)

FOREIGN PATENT DOCUMENTS

| CN | 1720466 A | 1/2006 |
| CN | 1916669 A | 2/2007 |

(Continued)

OTHER PUBLICATIONS

International Search Report, International Application No. PCT/CN2008/001900, dated Aug. 6, 2009, pp. 3.

(Continued)

*Primary Examiner* — Rochelle-Ann J Blackman

(57) ABSTRACT

The present invention related to an auto focus intraoral camera. The auto focus intraoral camera includes an illumination module for providing illuminating light, an imager, and a lens system for collecting light reflected from an object and focusing the light onto the imager, wherein said lens system further comprises at least one liquid lens including a vessel filled with a first liquid, and a second liquid being in contact with said first liquid, the first and second liquids being immiscible, of different optical indexes, and of substantially same density; wherein the lens system further includes a driver integrated circuit applying variable voltage to control the focal length of said lens. According to the present application, a compact auto focus intraoral camera with a small size and simple structure is provided, which decreases the camera complexity and improve the performance.

4 Claims, 3 Drawing Sheets

(56) References Cited

U.S. PATENT DOCUMENTS

| | | |
|---|---|---|
| 7,027,094 B2 | 4/2006 | Battles et al. |
| 7,245,440 B2 | 7/2007 | Peseux |
| 7,656,588 B2 | 2/2010 | Bae et al. |
| 7,801,589 B2 | 9/2010 | Tanikawa et al. |
| 7,808,717 B2 | 10/2010 | Kuiper et al. |
| 2005/0168579 A1 | 8/2005 | Imamura |
| 2006/0028734 A1* | 2/2006 | Kuiper et al. ............. 359/676 |
| 2006/0079728 A1* | 4/2006 | Kuiper et al. ............. 600/9 |
| 2006/0166162 A1 | 7/2006 | Ting |
| 2007/0156021 A1 | 7/2007 | Morse et al. |
| 2007/0236802 A1 | 10/2007 | Kohno |
| 2008/0079897 A1 | 4/2008 | Goldfain et al. |

FOREIGN PATENT DOCUMENTS

| | | |
|---|---|---|
| DE | 101 25 772 A1 | 12/2002 |
| EP | 1780575 A1 | 5/2007 |
| JP | 2006/509263 | 3/2006 |
| JP | 2007/167387 | 7/2007 |
| JP | 2007-538338 A | 12/2007 |
| JP | 2008-80117 A | 4/2008 |
| WO | WO2005/116908 | 12/2005 |
| WO | 2007/080521 A1 | 7/2007 |

OTHER PUBLICATIONS

Supplementary European Search Report, International Application No. PCT/CN2008/001900, dated Mar. 14, 2012, pp. 2.

* cited by examiner

AUTO FOCUS INTRAORAL CAMERA WITH LIQUID LENS

FIELD OF THE INVENTION

The invention relates generally to an intraoral imaging camera system. More specifically, the invention relates to a compact auto focus intraoral camera with liquid lens.

BACKGROUND OF THE INVENTION

Conventionally, in orthodontics, before treating teeth of a patient, photographs of the teeth of the patient are taken and stored as data before treatment, and a plan for the treatment is made on the basis of those photographs. In addition, during the course of orthodontic treatment, a dentist or an assistant takes photographs of the interior of an oral cavity to store them as data for enabling both the dentist and the patient to know the progress of the treatment and for use as presentation materials in academic conferences. Intraoral camera is known to be useful in the art. Images of the oral cavity can be displayed for purposes of diagnosis, treatment, patient education and the like.

Generally, intraoral camera comprises illumination module, lens module and electrical parts. Illumination module is used to provide enough light to illuminate the teeth. Polarized illumination can remove the specular reflection. For old intraoral camera, halogen lamp and optical fiber are adopted to transfer the light. Now, intraoral camera using white LED becomes more and more popular due to plurality advantages such as small size, long lifetime and high luminous flux.

Intraoral camera should be capable of performing intraoral acquisition, arch acquisition, smile acquisition, and so on. In this regard, the lens module of the camera must have a big DOF and wide FOV in a large range of working distance that is from 1 mm to infinity. The camera will be used in a large working distance range and must keep a big DOF. Then focus adjustment is necessary to guarantee the good image quality.

For most of the intraoral camera, focus adjustment is performed by manually adjusting the distance between the lens and sensor. But this method is not convenient for dentists to operate. Some of the intraoral camera will use small NA that can provide big DOF to replace focus adjustment. But small NA optical system cannot provide high resolution and will increase the luminous flux.

While such systems may have achieved certain degrees of success in their particular applications, there is a need to provide an intraoral camera having auto focus adjustment.

SUMMARY OF THE INVENTION

An object of the present invention is to provide an auto focus intraoral camera. The auto focus intraoral camera includes an illumination module for providing illuminating light, an imager, and a lens system for collecting light reflected from an object and focusing the light onto the imager, wherein said lens system further comprises at least one liquid lens including a vessel filled with a first liquid, and a second liquid being in contact with said first liquid, the first and second liquids being immiscible, of different optical indexes, and of substantially same density; wherein the lens system further includes a driver integrated circuit applying variable voltage to control the focal length of said lens.

This object is given only by way of illustrative example, and such object may be exemplary of one or more embodiments of the invention. Other desirable objectives and advantages inherently achieved by the disclosed invention may occur or become apparent to those skilled in the art. The invention is defined by the appended claims.

The compact intra oral camera according to the present application provides a small size and simple structure with liquid lens for auto focus, which decreases the camera complexity and improve the performance.

BRIEF DESCRIPTION OF THE DRAWINGS

The foregoing and other objects, features, and advantages of the invention will be apparent to those skilled in the art from the following more particular description of the embodiments of the invention, as illustrated in the accompanying drawings.

The elements of the drawings are not necessarily to scale relative to each other.

DETAILED DESCRIPTION OF THE INVENTION

Figure 1:
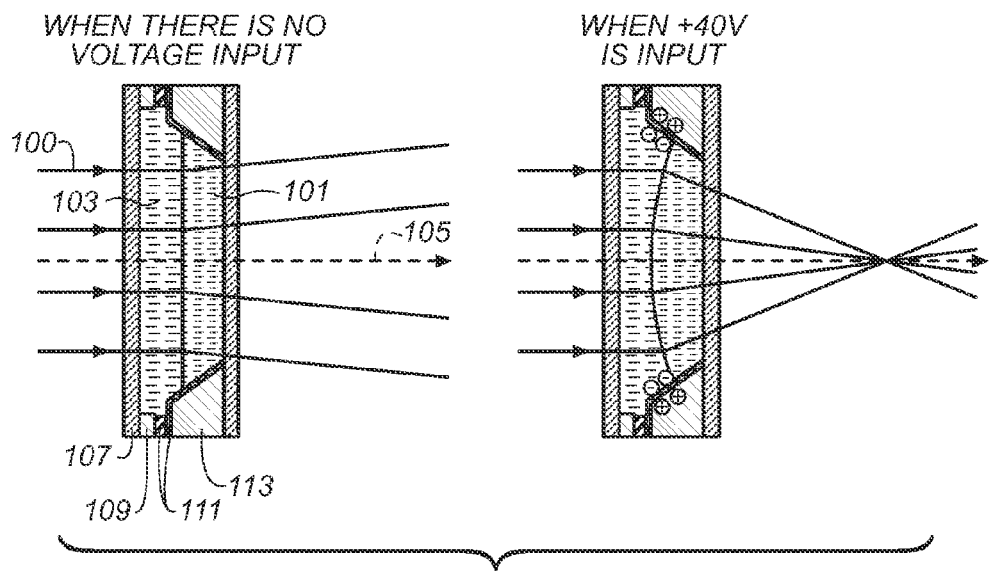
FIG. 1 shows the basic structure of liquid lens.

The following is a detailed description of the preferred embodiments of the invention, reference being made to the drawings in which the same reference numerals identify the same elements of structure in each of the several figures.

Referring to FIG. 1, the liquid lens 100 generally includes two kinds of liquids of equal density, which are sandwiched between two transparent windows 107 in a conical vessel. In this embodiment, one liquid is water 103, which is conductive, while the other, oil 101, acts as a lid, allowing the engineers to work with a fixed volume of water, and provides a measure of stability for the optical axis 105. Lens 100 further includes electrodes 109 and 113 insulated from oil 101 but in electrical contact with the water 103; and variable voltage can be selectively applied to the electrodes. Insulator 111 is deposited between electrodes 109 and 113 to separate them. The interface between oil 101 and water 103 will change its shape depending on the voltage applied across the conical structure. As shown in FIG. 1 (*a*), when zero volts are applied, the surface is flat. When the voltage is increased to 40 volts, the surface of oil 101 becomes highly convex, as figure FIG. 1 (*b*) shows. In this way, the liquid lens can attain the desired refraction power by means of changing the voltage applied on the electrodes.

Figure 2:
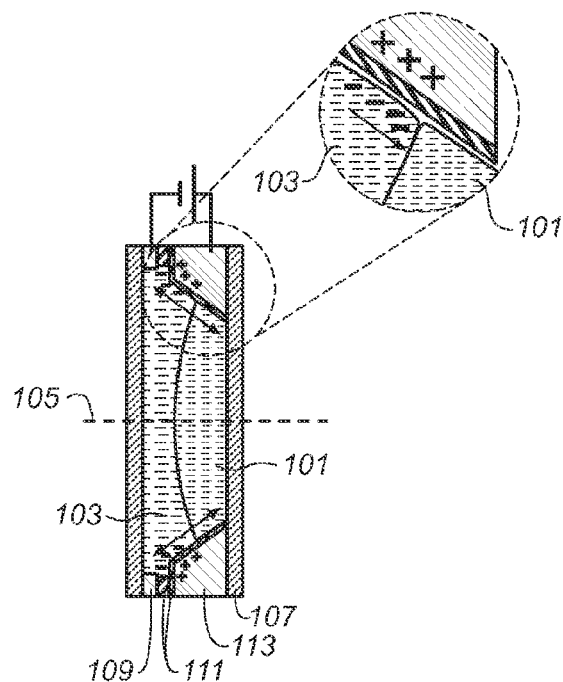
FIG. 2 shows the working principle of liquid lens.

FIG. 2 shows the working principle of the liquid lens 100 according to FIG. 1. The liquid lens 100 works based on the electro-wetting phenomenon described below: a water drop 103 is deposited on a substrate made of metal, covered by a thin insulating layer. The voltage applied to the substrate generating an electrostatic pressure to force the liquid change its shape so as to modify the contact angle of the liquid drop. Two iso-density liquids are employed by the liquid lens: one is insulator 101 while the other is conductor 103. The variation of voltage leads to a change of curvature of the liquid-liquid interface, which in turn leads to a change of the focal length of the lens.

Figure 3:
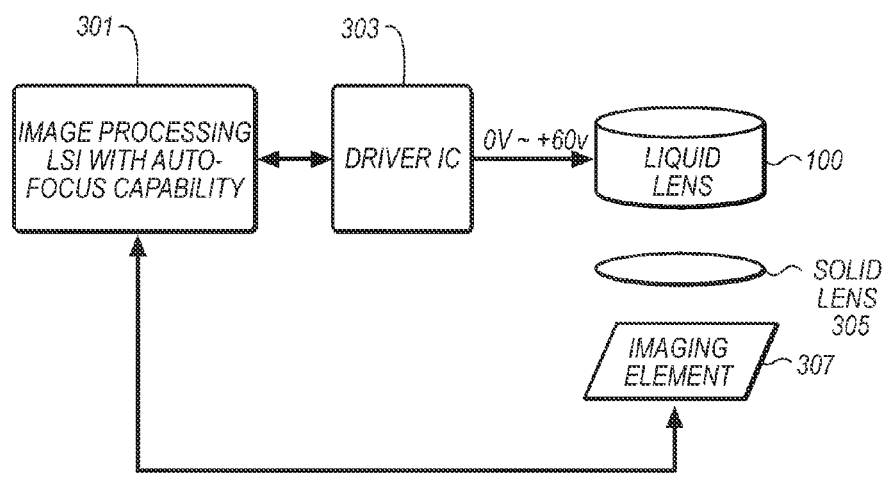
FIG. 3 shows the basic system structure of intraoral camera with liquid lens.

FIG. 3 is an exemplary auto focus intraoral camera comprising image processing LSI (Large Scale Integrated circuit) 301, driver IC (Integrated circuit) 303, liquid lens 100 and solid lens 305 as well as an imaging element 307. Wherein the driver IC 303 is used for providing variable voltage for the liquid lens 100, the imaging element 307 is used for capturing the images and the image processing LSI 301 is adopted for processing the images captured by the imaging element 305. The liquid lens 100 is used for auto focusing and the solid lens 305 here is main responsible for imaging. In other embodiments, the solid lens could also be replaced by a liquid lens.

Figure 4:
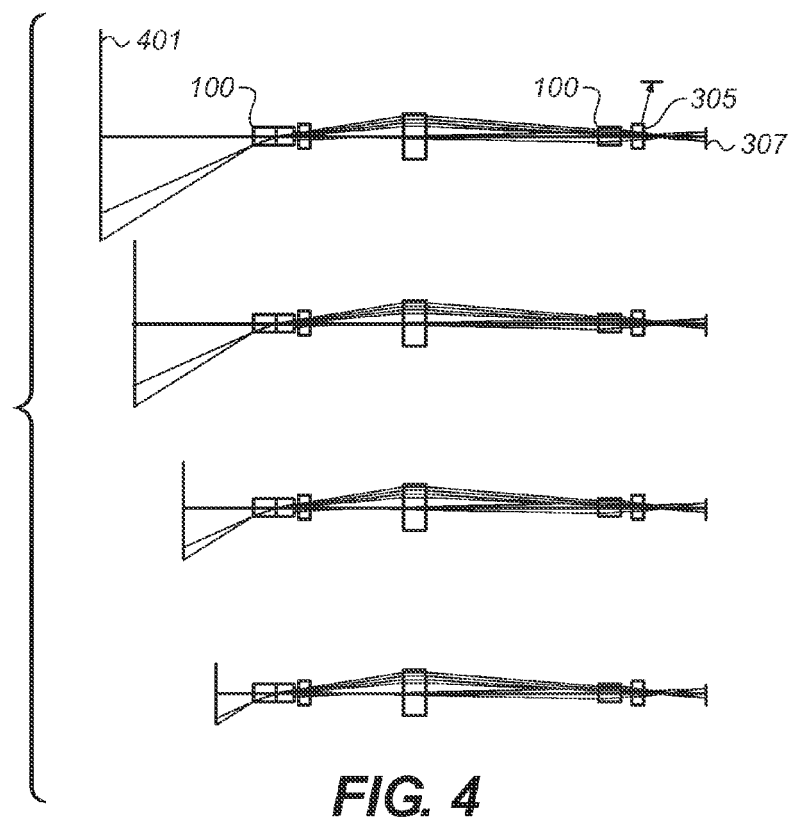
FIG. 4 shows an example of intraoral camera with liquid lens according to FIG. 3.

FIG. 4 illustrates an example of intraoral camera with liquid lens. As shown, lenses 100 and 305 are placed between the object 401 and the imaging element 307. And to be specific, the solid lens 305 is placed between the liquid lens 100 and the imaging element 307. In other words, the sequence thereof is the object 401, the liquid lens 100, the solid lens 305 and the imaging element 307. These parts are arranged in this way so that the liquid lens 100 could be adjusted for different working distances to help the solid lens 305 form the images on the imaging element 307. Here, solid lens is usually adopted as the imaging lens.

Figure 5:
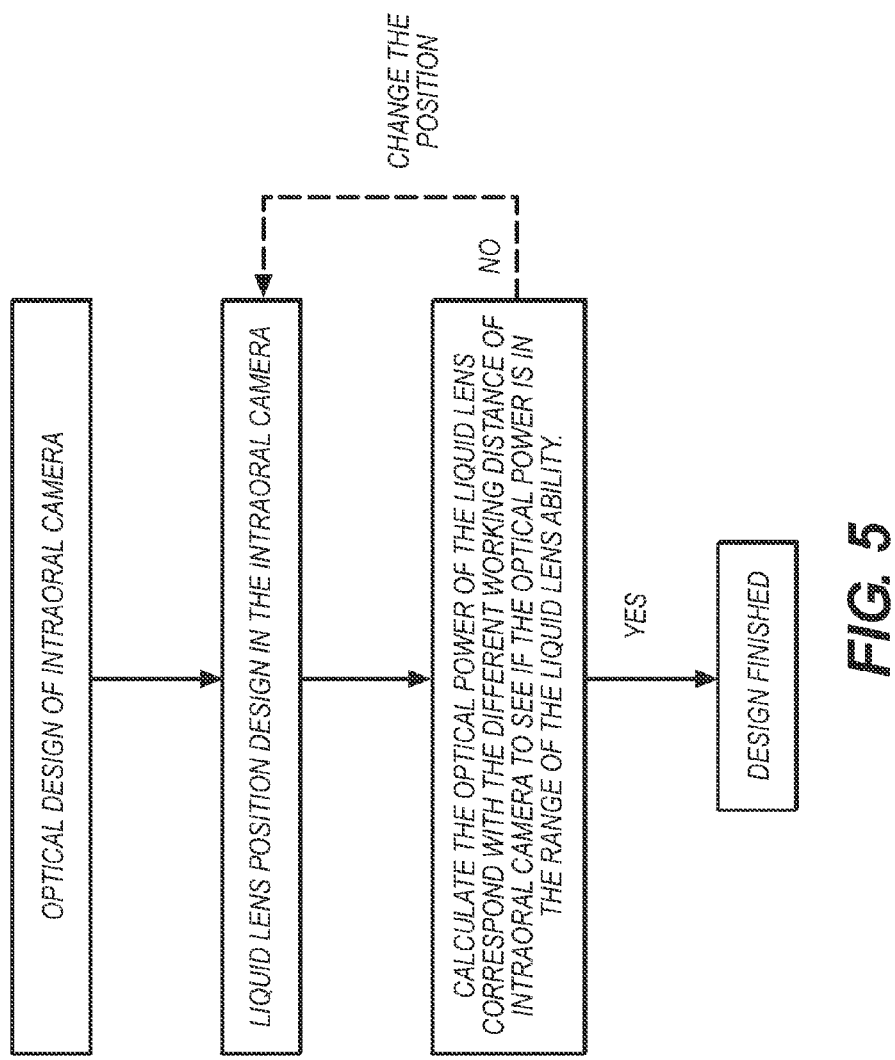
FIG. 5 shows the design flowchart of the intraoral camera according to FIG. 3.

FIG. 5 provides the flowchart of the optical design of intraoral camera. Firstly, the position of the liquid lens is determined in the intraoral camera; then the optical power of the liquid lens is calculated correspond with the different working distance of intraoral camera to determine whether the optical power is in the range of the liquid lens ability. If the optical power out of the range, then the position of the liquid lens should be relocated and then recalculate the optical power for the determination. If the optical power does succeed the range, which means the position is proper, then the present design goes to end.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. An auto focus intraoral camera comprising:
    an illumination module for providing illuminating light;
    an imager; and
    a lens system for collecting light reflected from an object and focusing the light onto the imager, wherein the lens system comprises:
        at least one solid imaging lens,
        at least one liquid lens including a vessel filled with a first liquid, and a second liquid being in contact with the first liquid, the first and second liquids being immiscible, of different optical indexes, and of substantially same density; and
        a driver integrated circuit applying variable voltage to control the focal length of the at least one liquid lens, wherein the at least one liquid lens is located between the at least one solid imaging lens and the object and is movable along an optical axis to adjust a working distance toward the object.

2. The auto focus intraoral camera as set forth in claim 1 wherein the first liquid is a conductor and the second liquid is an insulator.

3. The auto focus intraoral camera as set forth in claim 1 wherein said illumination module includes a LED.

4. The auto focus intraoral camera as set forth in claim 1 wherein the imager is located on the optical axis.

* * * * *